United States Patent [19]

Poore

[11] Patent Number: 5,387,229
[45] Date of Patent: Feb. 7, 1995

[54] MULTI-SENSOR CARDIAC PACEMAKER WITH SENSOR EVENT RECORDING CAPABILITY

[75] Inventor: John W. Poore, South Pasadena, Calif.

[73] Assignee: Pacesetter, Inc., Sylmar, Calif.

[21] Appl. No.: 7,648

[22] Filed: Jan. 21, 1993

[51] Int. Cl.[6] ............................................. A61N 1/36
[52] U.S. Cl. ..................................................... 607/18
[58] Field of Search ..................... 607/61, 10, 17, 26, 607/30, 32; 128/903

[56] References Cited

U.S. PATENT DOCUMENTS

5,081,987  1/1992  Nigam .................................. 607/30

Primary Examiner—Lee S. Cohen
Assistant Examiner—Marianne Parker
Attorney, Agent, or Firm—Lisa P. Weinberg; Malcolm J. Romano

[57] ABSTRACT

A rate-response pacemaker includes a plurality of sensors that each sense a physiologic-related parameter suggestive of the physiological needs of a patient, and hence, indicative of the pacing rate at which the rate-responsive pacemaker should provide pacing pulses on demand. The pacemaker includes appropriate selection circuitry for selecting which of the sensor parameters, or weighted combinations thereof, should be used as the sensor indicated rate (SIR) signal to control the pacing rate of the pacemaker at any given time. The pacemaker also includes a memory circuit for selectively storing the sensor parameters from each of the plurality of sensors. The stored sensor parameters may thereafter be downloaded from the pacemaker memory and evaluated in non-real time with the various sensor parameters assuming different weighting (scaling) factors and different processing parameters (e.g., filtering), thereby allowing an optimum combination of the sensor parameters to be determined without requiring repeated trials by the patient.

16 Claims, 7 Drawing Sheets

MULTI-SENSOR CARDIAC PACEMAKER WITH SENSOR EVENT RECORDING CAPABILITY

BACKGROUND OF THE INVENTION

1. Field of the Invention

The present invention relates to implantable medical devices and methods, and more particularly, to a rate-responsive pacemaker that includes a plurality of sensors for sensing a corresponding plurality of physiologic-related parameters indicative of an appropriate pacing rate, and to a method of operating such a pacemaker to optimize which of the plurality of sensed physiologic-related parameters, or which combination thereof, should be used to define the pacing rate of the pacemaker at any given time.

The heart is a pump that pumps life-sustaining blood through a patient's body in order to carry oxygen to, and remove carbon dioxide from, the tissue cells located throughout the body. In a healthy patient, i.e., a patient having a normal heart, the rate at which the blood is pumped through the body, which rate is determined by the heart rate, increases or decreases as the physiologic needs of the patient increase or decrease. That is, as the patient's body cells need more oxygen in order to do more work (as might occur, for example, if the patient starts to exercise), the heart rate increases in order to pump more blood, and hence more oxygen, to the cells. If insufficient oxygen is available (which oxygen is picked up by the blood in the lungs), then the respiration rate may also increase in order to increase the intake of oxygen. As the work being done by the patient's body is completed, and as the demand for oxygen at the body cells decreases, then the heart rate slows, providing less blood flow, and hence less oxygen, to the cells. In this manner, the healthy heart maintains an optimum heart rate that keeps the body cells fed with a sufficient supply of oxygen to do whatever work they may be called upon to do. Maintaining an adequate blood flow to supply the body cells with the proper amount of oxygen is referred to as "hemodynamics."

A pacemaker is an implantable medical device that aids a patient with a diseased or damaged heart to maintain an adequate blood flow through his or her body. The pacemaker controls the rate at which the patient's heart beats, and thus controls the rate at which blood flows through the patient's body. To accomplish this function, the pacemaker includes sensing circuits that sense the natural heartbeat, e.g., the depolarization of the atria (as manifest by the occurrence of a P-wave), or the depolarization of the ventricles (as manifest by the occurrence of an R-wave, or QRS complex). If a natural heartbeat is not sensed within a prescribed time interval since the last heartbeat, then a stimulation pulse (or "pacing pulse") is generated and delivered to the heart in order to stimulate the cardiac muscle tissue to contract. The prescribed time interval during which the pacemaker monitors the heart is typically referred to as the "escape interval." If a natural heartbeat is sensed before the escape interval times-out, then the pacemaker timing circuits are reset, allowing the next cardiac cycle to begin, during which a new escape interval is started, and no stimulation pulse is generated. In this way, the pacemaker provides stimulation pulses to the heart only when needed, i.e., only when a natural heartbeat does not occur during the escape interval. Providing stimulation pulses in this manner, i.e., only when needed, is referred to as providing stimulation pulses "on demand."

Most modern pacemakers allow the escape interval to be programmed to a desired value. Hence, the rate at which the pacing pulses are provided to the patient's heart can be programmed to a desired value. The rate at which pacing pulses are provided is typically referred to as the "pacing rate." So long as the natural heart rate of the patient exceeds the pacing rate, no stimulation pulses are generated by the pacemaker when the pacemaker is operating in a demand mode of operation (i.e., in a mode where stimulation pulses are provided on demand). However, as soon as the natural heart rate slows to a value below the pacing rate, the pacemaker generates whatever stimulation pulses are needed to maintain the heart rate at the pacing rate.

A rate-response pacemaker is a pacemaker that automatically adjusts the pacing rate as a function of a sensed physiologic-related parameter in order to achieve a hemodynamically beneficial pacing rate. Like conventional pacemakers, rate-responsive pacemakers provide pacing pulses to a patient's heart on demand (i.e., only when needed) in order to maintain the heart rate at the pacing rate. Unlike conventional pacemakers, a rate-responsive pacemaker includes a sensor that senses a physiologic-related parameter of the patient, e.g., physical activity, and adjusts the pacing rate, within prescribed limits, as a function of the sensed physiologic-related parameter. For example, suppose a patient has a rate-responsive pacemaker that uses an activity sensor, e.g., a piezoelectric crystal, to sense the physical activity of the patient. If the patient is at rest, the activity sensor fails to sense significant physical activity, and pacing pulses are provided on demand at a minimum rate, e.g, 70 pulses per minute (ppm), thereby assuring that the patient's heart rate is at least 70 beats per minute (bpm), which rate is usually sufficient to meet the physiological demands of the patient while at rest. If the patient is exercising, the activity sensor senses significant physical activity, and pacing pulses are provided on demand at a rate commensurate with the sensed physical activity, which rate may vary, e.g., from 70 ppm to 130 ppm, or higher. Thus, the heart rate of the patient, as controlled by the rate-responsive pacemaker, increases or decreases within prescribed limits as a function of the sensed physiologic-related parameter, thereby mimicking the hemodynamic response of a healthy heart in responding to changes in the physiological needs of the patient.

Rate-responsive pacemakers are known in the art that use a wide variety of physiologic-related sensors. See, e.g., U.S. Pat. No. 4,140,132 issued to Dahl (piezo activity sensor); U.S. Pat. No. 4,485,813 issued to Anderson et al. (piezo activity sensor); U.S. Pat. No.4,712,555 issued to Thornander et al. (depolarization time interval); U.S. Pat. No. 4,399,820 issued to Wirtzfeld et al. (blood oxygen sensor). Other types of physiologic-related sensors include body temperature sensors; blood Ph sensors; and respiration rate sensors. Note: as used herein, the term "physiologic-related sensor" refers to any sensor that senses a parameter that provides some indication of a change in the physiologic needs of a patient, whether the sensed parameter is a true physiological parameter or not. For example, the amount of oxygen in the blood is a true physiologic parameter. In contrast, the physical activity of a patient as sensed using a sensor that senses pressure on or acceleration of the pacemaker is not a true physiologic parameter.

Nonetheless, physical activity sensed with such a sensor provides some indication or suggestion that the physiological needs of the patient may be changing.

Rate-responsive pacemakers are also known in the art that use a plurality of sensors, and that then combine or otherwise process all of the outputs of the plurality of sensors in order to arrive at a single output that controls the rate at which the pacemaker provides stimulation pulses on demand. See, e.g, U.S. Pat. No. 4,722,342 issued to Amundson; and U.S. Pat. No. 5,097,831 issued to Lekholm. Rate-responsive pacemakers using a plurality of sensors are referred to herein as multi-sensor rate-responsive pacemakers.

In a multi-sensor rate-responsive pacemaker, the relationship of the various sensor outputs to the pacing rate is typically a weighted combination of the sensor outputs. The weighted combination is then used to compute or to look up a corresponding pacing rate. The difficulty with this weighted combination approach is that the weighting of a given sensor output may have hemodynamic significance that varies with time and in relation to the magnitude of other sensor outputs. For example, consider a combination of sensors that includes an activity sensor (which typically measures movement or acceleration of, or pressure on, the pacemaker) and an oxygen saturation sensor (which measures the saturated oxygen content of the blood). Activity is measurable at the immediate onset of exercise or physical activity, whereas the oxygen saturation is not. Rather, the oxygen saturation has a latency associated therewith due to the transportation time of oxygen depleted blood from the muscle cells demanding more oxygen and the heart wherein the oxygen saturation sensor is typically located. Activity, although immediately available, is prone to false positive responses because it is not a true physiologic parameter of the body. The oxygen saturation measurement, on the other hand, not being immediately available because of the above-described latency, is a true physiologic parameter that is directly related to the heart rate except for the latency. Thus, without factoring in the latency of the oxygen saturation measurement, there is no way to correctly weight the combination of the activity measurement and the oxygen saturation measurement. Hence, what is needed is a dynamic weighting approach wherein the sensed activity is more heavily weighted during the onset or acceleration of such sensed activity, and the sensed oxygen saturation is more heavily weighted during intervals of more stable sensed activity or at other times when the oxygen saturation parameter provides a better indication of the needed heart rate. More generally, what is needed for a multi-sensor rate-responsive pacemaker is a dynamic weighting or selection criteria wherein the sensor output that best represents the true physiologic needs of the patient at a given time is selected or weighted more heavily at such given time, and is not-selected or lightly weighted during other times, thereby achieving a more hemodynamically beneficial pacing rate.

The above-mentioned difficulties of optimally weighting a plurality of sensor parameters within a multi-sensor rate-responsive pacemaker are further heightened when individual patient variations are considered. That is, the latency time associated with a given oxygen saturation sensor output may be quite different in one patient than it is in another. Hence, the optimal dynamic weighting of the plural sensor parameters for one patient may be quite different than the optimal dynamic weighting of the same plural sensor parameters for another patient. What is thus needed is a way to safely and easily assess which of plural sensor outputs, or combinations of plural sensor outputs, provides the most beneficial hemodynamic results for a given patient.

Because each individual patient is so different, the only way to assure that the plurality of sensor signals used with a multi-sensor rate-responsive pacemaker have been optimally weighted and combined for a particular patient is to combine or weight the sensor signals one way, try out the pacemaker using such combination or weighting factors (i.e., perform a trial or test), make adjustments in the combination or weighting factors of the sensor signals based on the results of the trial, perform another test or trial, and so forth. Unfortunately, such "trial and error" process requires a great deal of patient and physician interface, which means it is very costly in terms of time and money. Hence, what is needed is an alternate way to perform such patient tests and trials that is less expensive to use, and that minimizes the interface between the physician and the patient to a short time.

SUMMARY OF THE INVENTION

Accordingly, it is a general feature of the invention to provide a multi-sensor cardiac pacemaker wherein the aforementioned problems are eliminated, and the aforementioned needs are met.

Another and more specific feature of the invention is to provide a multi-sensor rate-responsive pacemaker that uses signals from a plurality of sensors to determine the sensor indicated rate (SIR) signal used by the pacemaker for its rate-responsive functions so as to achieve a more hemodynamically beneficial pacing rate.

A further feature of the invention is to provide a multi-sensor rate-responsive pacemaker wherein a weighted combination of a plurality of sensor signals is automatically selected as the pacemaker's SIR signal, and, wherein the amount of weighting given one sensor signal at any given time varies as a function of which sensor signal best typifies the physiologic need of the patient at that time.

Yet an additional feature of the invention is to provide a multi-sensor rate-responsive pacemaker wherein each of the plurality of sensor signals is selectively stored in a memory circuit of the pacemaker and may thereafter be downloaded to an external programmer, or equivalent external processing/computing device, for non-real time processing, thereby enabling a non-real time analysis of different combinations of the sensor signals, including different weighting factors, in arriving at a hemodynamically beneficial SIR rate.

Still another feature of the invention is to provide a multi-sensor rate-responsive pacemaker using both an oxygen saturation sensor (to measure the oxygen saturation level of the patient's blood) and an activity sensor (to measure the physical activity level of the patient), and to select an SIR signal that is a weighted combination of the oxygen saturation sensor signal and the activity sensor signal, with the activity sensor signal being heavily weighted during the initial onset or acceleration of increased physical activity (e.g., exercise), and with the oxygen saturation sensor signal being heavily weighted at other times (e.g., rest, stable physical activity, or return to rest).

An additional feature of the invention is to provide a way to safely and easily assess which of plural sensor outputs, or combinations of plural sensor outputs, used by a multi-sensor rate-responsive pacemaker provides the most hemodynamically beneficial results for a given patient at a given time.

Yet another feature of the invention is to provide a more effective, less expensive way to perform the patient tests and trials that are needed to assess whether a given selection or weighting of plural sensor output signals is best suited for a given patient.

The above and other features are provided in a rate-responsive pacemaker that includes a plurality of sensors for sensing a plurality of sensor parameters suggestive of the physiological needs of a patient, and hence indicative of the pacing rate at which the rate-responsive pacemaker should provide pacing pulses on demand. More particularly, the invention provides specific selection circuitry and specific selection criteria for determining which of the plurality of sensor parameters, or which combinations thereof, should be used to control the pacing rate of the pacemaker at any given time so as to achieve a hemodynamically beneficial pacing rate.

In accordance with one aspect of the invention, the plurality of sensor parameters are each monitored and stored within a memory circuit of the implantable pacemaker while the patient performs an exercise protocol. After the exercise protocol is completed, the stored sensor parameters are downloaded from the pacemaker memory through a telecommunicative link established between the implantable pacemaker and an external programmer and/or computer. The combined response of the pacemaker's rate can then be evaluated in non-real time with the various sensor parameters assuming different weighting (scaling) factors and different processing parameters (e.g., filtering), thereby allowing an optimum combination of the sensor parameters to be determined without requiring repeated trials by the patient.

One embodiment of the present invention may be characterized as an implantable rate-responsive pacemaker. Such pacemaker includes: (1) a plurality of sensors, each being adapted to sense a respective physiologic-related parameter of a patient and to generate a physiological signal indicative of such sensed physiologic-related parameter; (2) a sense amplifier that senses natural contractions of the patient's heart; (3) a pulse generator that selectively generates stimulation pulses responsive to a pacing signal and delivers such stimulation pulses to the patient's heart; (4) control/timing means for defining a first escape interval and starting the escape interval during a sensed or paced cardiac cycle, and generating the pacing signal at the end of the first escape interval unless a natural contraction of the patient's heart is sensed by the sense amplifier prior to the conclusion of the first escape interval, in which case the first escape interval is reset and no pacing signal is generated; (5) memory means for selectively storing the physiological signal from each of the plurality of sensors and other sensor parameter signals; and (6) sensor processing means coupled to the control/timing means and the memory means for generating a sensor indicated rate (SIR) signal, which SIR signal is used by the control/timing means to define the duration of the first escape interval, and which SIR signal comprises a specified combination of the physiological signals from the plurality of sensors and other sensor parameter signals stored in the memory means. Thus, such rate-responsive pacemaker generates stimulation pulses on demand at a rate determined by the SIR signal.

Another embodiment of the invention may be characterized as a rate-responsive pacing system. Such rate-responsive pacing system includes an implantable rate-responsive pacemaker as described in the paragraph above. Such pacemaker further includes telemetry means for establishing a communication link between the memory means and an external receiver; and an external programmer device that includes the external receiver. The external programmer device further includes means for selectively downloading the physiological signals stored in the memory means of the pacemaker, and processing means for combining the physiological signals with different weighting factors in order to arrive at a combined physiological signal that is used to generate the SIR signal. Thus, with the aid of the external programmer device, or equivalent processor, various combinations of the physiological signals may be analyzed or tested in order to determine an optimum combination thereof that may thereafter be used by the sensor processing means to define the SIR signal.

Yet an additional embodiment of the invention may be viewed as a method of determining an optimum sensor indicated rate (SIR) signal for use within a multi-sensor rate-responsive pacemaker implanted in a patient. Such method requires an implantable multi-sensor rate-responsive pacemaker as described above, i.e., a pacemaker that includes at least: a plurality of sensors, each being adapted to sense a physiologic-related parameter of the patient and to generate a physiological signal indicative of such sensed physiologic-related parameter; a sense amplifier that senses natural contractions of the patient's heart; a pulse generator that selectively generates stimulation pulses on demand at a rate determined by the SIR signal; and a memory circuit. The method includes the following steps: (a) having the patient perform a specified exercise protocol; (b) sampling each of the plurality of sensors to obtain a respective sampled physiological signal while the patient is performing the specified exercise protocol; (c) storing each of the respective sampled physiological signals in the memory circuit as the sampled physiological signals are obtained; (d) terminating the exercise protocol; (e) downloading the stored physiological signals from the pacemaker memory circuit to an external programmer; (f) evaluating the downloaded physiological signals and defining the SIR signal to be a specified function thereof; and (g) uploading the specified function to the memory circuit of the pacemaker. Thus, using this method, the specified function that defines an optimum SIR signal is advantageously determined by subjecting the patient to a single exercise protocol.

BRIEF DESCRIPTION OF THE DRAWINGS

The above and other aspects, features and advantages of the present invention will be more apparent from the Detailed Description of the Invention presented in conjunction with the following drawings, wherein:

FIGS. 7-1 and 7-2 show a flowchart that illustrates the operation of a pacemaker having a sensor event recording feature in accordance with the invention;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Applicant's copending application, filed concurrently herewith, entitled "Multi-Sensor Rate-Responsive Pacemaker and Method of Operating Same" (hereafter referred to as the "copending application"), describes how the physiological signals from a plurality of sensors of a multi-sensor rate-responsive pacemaker may be combined in order to arrive at an appropriate sensor indicated rate (SIR) signal that may thereafter be used in controlling the pacing rate of the pacemaker. Such copending application is incorporated herein by reference. One embodiment described in such copending application utilizes an oxygen saturation sensor and an activity sensor and shows how the signals from such sensors are combined in accordance with a prescribed weighting function (shown in FIG. 7 of the copending application) in order to arrive at a hemodynamically beneficial pacing rate.

The present application also describes how the physiological signals obtained from a plurality of sensors in a rate-responsive pacemaker may be combined in order to arrive at a hemodynamically beneficial pacing rate. Unlike the copending application, however, which presumes a desired weighting function (such as is shown in FIG. 7 of the copending application) has already been defined for a given plurality of physiological sensors, the present application focuses on how such a weighting function may be optimally determined using minimal testing and physician-client interface.

The present invention thus comprises an implantable rate-responsive pacemaker that uses a plurality of sensors to sense a corresponding plurality of physiologic-related parameters. Each of the sensors generates a raw sensor signal that can be appropriately processed to derive a sensor indicated rate (SIR) signal for use by the pacemaker in determining its pacing rate, i.e., the rate at which it provides pacing pulses on demand to a patients heart. A rate-responsive pacemaker made in accordance with the present invention may be either a dual-chamber pacemaker or a single-chamber pacemaker, although the invention is described in FIGS. 1 and 2 below as a dual-chamber pacemaker. In order to better appreciate and understand the present invention, an overview of the basic operation of a rate-responsive pacemaker is first presented.

Figure 1:
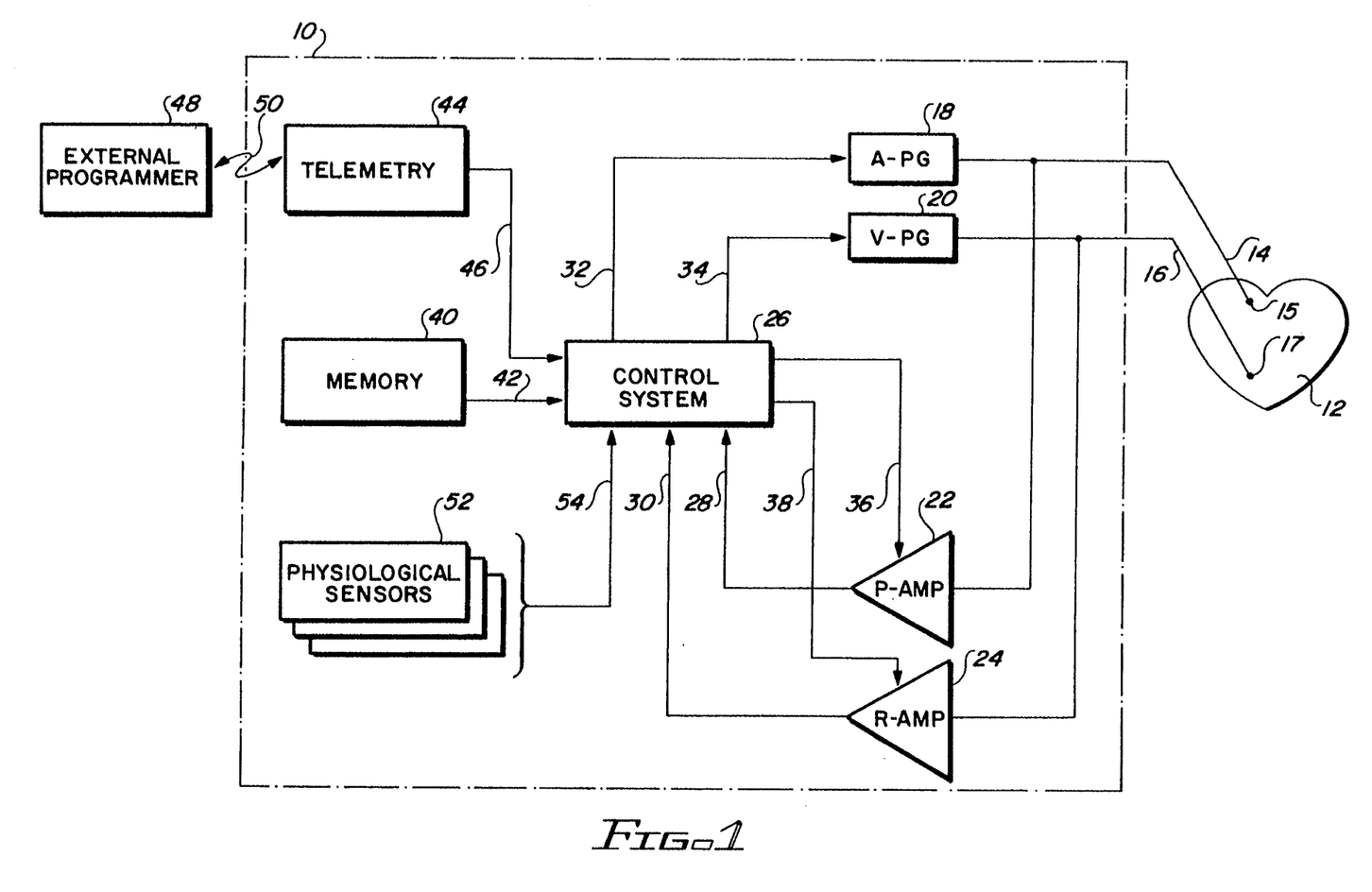
FIG. 1 shows a functional block diagram of a multi-sensor rate-responsive pacemaker made in accordance with the present invention.

Referring to FIG. 1, a simplified block diagram of a dual-chamber pacemaker 10 is illustrated. The pacemaker 10 is coupled to a heart 12 by way of leads 14 and 16, the lead 14 having an electrode 15 that is in contact with one of the atria of the heart, and the lead 16 having an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual-chamber pacemaker 10 is a timing/control system 26. The timing/control system 26 (referred to hereafter as simply the control system 26) receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. The atrial stimulation pulse is referred to simply as the "A-pulse," and the ventricular stimulation pulse is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

Still referring to FIG. 1, the pacemaker 10 also includes a memory circuit 40 that is coupled to the control system 26 over a suitable data/address bus 42. This memory circuit allows certain control parameters, used by the control system 26 in controlling the operation of the pacemaker, to be programmably stored and modified, as required, in order to customize the pacemaker's operation to suit the needs of a particular patient. Such parameters include the basic timing intervals used during operation of the pacemaker, such as the programmed escape interval (EI). Further, as explained more fully below, sensor signals (or other signals sensed during the operation of the pacemaker) may be stored in the memory 40 for later retrieval and analysis.

A telemetry circuit 44 is further included in the pacemaker 10. This telemetry circuit 44 is connected to the control system 26 by way of a suitable command/data bus 46. In turn, the telemetry circuit 44, which is included within the implantable pacemaker 10, is selectively coupled to an external programming device 48 by means of an appropriate communication link 50 whenever there is a need to transfer information to or from the pacemaker. The communication link 50 may be any suitable electromagnetic link, such as an RF (radio frequency) channel. Advantageously, through the external programmer 48 and the communication link 50, desired commands may be sent to the control system 26. Similarly, through this communication link 50 and the programmer 48, data signals (either held within the control system 26, as in a data latch, or stored within the memory 40) may be remotely received from the pacemaker 10. In this manner, non-invasive communications can be established with the implanted pacemaker 10 from a remote, non-implanted, location.

The pacemaker 10 in FIG. 1 is referred to as a dual-chamber pacemaker because it interfaces with both the atria and the ventricles of the heart. Those portions of the pacemaker 10 that interface with the atria, e.g., the lead 14, the P-wave sense amplifier 22, the A-pulse generator 18, and corresponding portions of the control system 26, are commonly referred to as the atrial channel. Similarly, those portions of the pacemaker 10 that interface with the ventricles, e.g., the lead 16, the R-wave sense amplifier 24, the V-pulse generator 20, and corresponding portions of the control system 26, are commonly referred to as the ventricular channel. A single-chamber pacemaker, in contrast, has only an atrial channel or a ventricular channel. Most dual-chamber pacemakers can be programmed to operate in a single-chamber mode of operation.

In accordance with the present invention, the pacemaker 10 further includes a plurality of physiological sensors 52, each of which is connected to the control system 26 of the pacemaker over a suitable connection line 54. While these sensors 52 are illustrated in FIG. 1 as being included within the pacemaker 10, it is to be understood that at least some of the sensors may be external to the pacemaker 10, yet still be implanted within or carried by the patient. A common type of sensor is an activity sensor, such as a piezoelectric crystal, mounted to the case of the pacemaker. Other types of physiologic sensors that may be included in the plurality of sensors 52 include sensors that sense the oxygen content of blood, respiration rate, pH of blood, blood temperature, body motion, the depolarization time interval; the repolarization time interval, the pre-ejection time interval, and the like. The type of sensors used is not critical to the present invention. Any combination of sensors, each capable of sensing some physiologic-related parameter that suggests the rate at which the heart should be beating can be used.

The sensors 52 are used with the rate-responsive pacemaker 10 in order to adjust the rate (escape interval) of the pacemaker in a manner that tracks the physiological needs of the patient. A selected one or selected ones of the plurality of raw sensor signals are selected and processed in order to generate a sensor indicated rate (SIR) signal. Once the appropriate raw sensor signal, or weighted combination of a plurality of raw sensor signals, has been selected or generated, such selected signal(s) may then be processed by the rate-responsive pacemaker in conventional manner, as taught, e.g., in U.S. Pat. Nos. 4,712,555; 4,809,697; 4,940,052; or 4,940,053; which patents are incorporated herein by reference. Further processing of the sensor parameters of a rate-responsive pacemaker is disclosed in U.S. patent application Ser. No. 07/844,818, filed Mar. 2, 1992, entitled "Method and System for Automatically Adjusting the Sensor Parameters of a Rate-Responsive Pacemaker," assigned to the same assignee as the present invention, also incorporated herein by reference.

Figure 2:
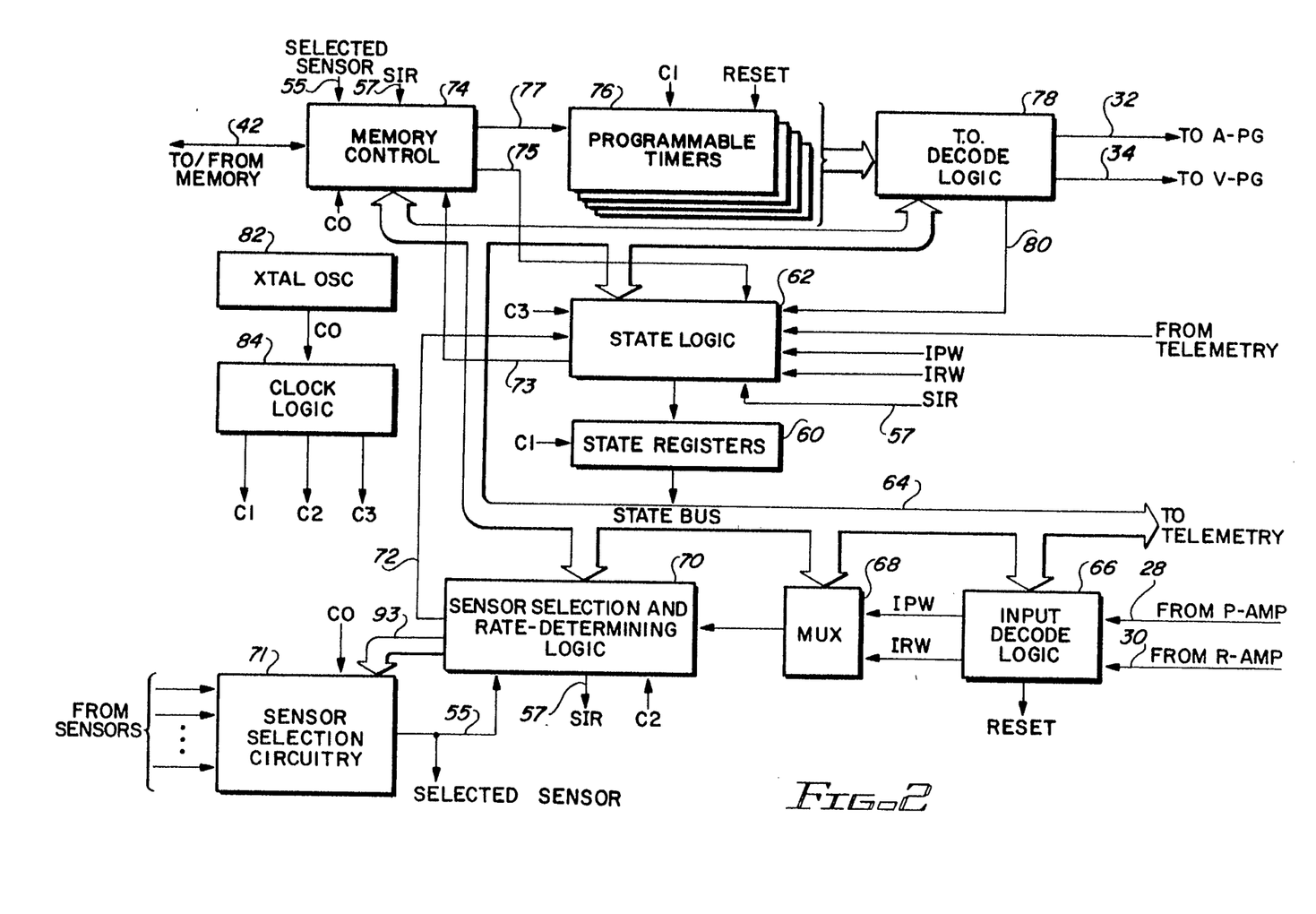
FIG. 2 is a functional block diagram of one embodiment of the control system of FIG. 1.

Referring next to FIG. 2, a block diagram of one embodiment of the control system 26 of the pacemaker 10 is illustrated. It is noted that other embodiments of a control system 26 may also be utilized, such as a microprocessor-based control system. A representative microprocessor-based system is described, for example, in U.S. Pat. No. 4,940,052, entitled "Microprocessor Controlled Rate-Responsive Pacemaker Having Automatic Threshold Adjustment," also incorporated herein by reference.

The control system shown in FIG. 2 is based on a state machine wherein a set of state registers 60 define the particular state of the pacemaker at any instant in time. In general, and as an overview of state machine operation, each state, by design, causes a certain activity or function to be carried out. Several states are executed in a sequence during a given cardiac cycle. The sequence of states that is executed in a particular cardiac cycle is determined by the particular events that occur, such as the sensing of a P-wave or an R-wave, as well as the current state, as certain states can only be entered from certain other states. Only one state can exist at any instant of time, although several different state machines (or control systems) may operate in parallel to control diverse functions. For example, the telemetry circuit 44 (FIG. 1) preferably utilizes its own state machine. This telemetry circuit state machine operates essentially independent of the control system state machine of FIG. 2.

At the heart of the control system 26 is the state logic 62. It is the state logic that controls the "state" of the state registers 60, and hence the function or operation that will next be carried out by the system. The state logic 62 receives as inputs the current state of the state registers, made available over a state bus 64 (which state bus directs the state of the system to several sections of the control system), as well as other signals indicating the current status of the system or events that have occurred. The output signals from the P-AMP 22 (FIG. 1) and the R-AMP 24 (FIG. 1) are directed to an input decode logic circuit 66. This circuit generates appropriate logic signals "IPW" (inhibiting P-wave) and "IRW" (inhibiting R-wave) that are selected by a multiplexer 68 and sent to rate-determining logic 70. These signals are also sent to the state logic 62. The function of the rate-determining logic 70 is to determine the rate at which either the IPW or IRW signals are occurring. A signal representative of this rate is sent, as an output signal from the rate determining logic 70, to the state logic 62 over signal line 72.

Rate-determining logic 70 further receives a selected sensor signal, or samples from several selected sensor signals, from the sensor selection circuitry 71 over signal line 55. Such signal is referred to as the "selected sensor" signal in FIG. 2. Depending upon the particular state of the system, as defined by the state registers 60, and as made available to the rate-determining logic 70 over the state bus 64, such signal or signals are appropriately processed, in accordance with a specific SIR-defining function, and converted to an appropriate SIR signal. The SIR signal is then sent to the state logic 62 and/or to a memory control circuit 74 over signal line 57, where it is used to set the pacing rate (e.g., to define the appropriate escape interval) of the pacemaker.

Still referring to FIG. 2, the memory control circuit 74 provides the needed interface between the circuits of the control system 26, the memory 40 (FIG. 1), the selected sensor signal 55, and/or the SIR signal. This memory control circuit may be any conventional memory access circuit that sends or receives data signals to or from the memory 40 at a specified address. Data retrieved from memory 40 may be sent to either the state logic 62 (over signal line(s) 75) or one or more programmable timers 76 (over signal line(s) 77). Data sent to memory 40 may be either the current state of the system (obtained off of the state bus 64); the selected sensor signal 55 and/or the SIR signal (which signals may be stored in a histogram, or the like); or other selected signals from the state logic (as made available over signal line(s) 78).

The programmable timers 76 define one or more prescribed time intervals, the length of which is set by the signal(s) received from the memory control 74 over signal line(s) 77. The starting point for a given time interval begins coincident with the start of the current state, as obtained from the state bus 64. The timers 76 further generate respective time-out (T.O.) signals when the prescribed time interval has elapsed. During a given prescribed time interval, the timing function may be reset by a reset signal, typically obtained from the input decode logic 66, although some states (as obtained from the state bus 64) may also effectuate an immediate reset of one or more of the timers 76. The time-out signals are sent to time-out decode logic 78. It is the function of the time-out decode logic to generate the appropriate trigger signals that are sent to the A-pulse generator 18 or the V-pulse generator 20 (FIG. 1). Further, an appropriate logic signal(s) is sent to the state logic 62 by the time-out decode logic 78 over signal line(s) 80 in order to notify the state logic that the respective trigger signals have been generated.

An oscillator 82, preferably a crystal-controlled oscillator, generates a basic clock signal CO that controls the operation of the system logic. This clock signal CO is sent to clock logic circuits 84, where other appropriate clock signals, such as clock signals C1, C2, and C3, are generated, all derived from the basic clock signal CO. These clock signals are distributed throughout the control system 26 in order to appropriately synchronize the various events and state changes that occur within the pacemaker. The rate of the basic clock signal CO is not critical to the present invention. In general, a rate of 25–40 Khz for the basic clock rate C0 is adequate. This rate provides a basic time increment of 25–40 microseconds each clock cycle, and this is more than enough time to effectively control the pacemaker operation. A faster basic clock rate may be used, however, by the memory control 74 in order to speed up the data signal transfer between the control system 26 and the memory 40, although for most pacemaker operations, a fast data signal transfer rate is not essential.

In operation, the control system of FIG. 2 thus starts at an initial state, wherein the state registers 60 assume a prescribed value that defines the initial state. For example, assuming four flip flops are used for the state registers 60, an initial state might be "1000" (hexadecimal "8") wherein the first flip flop assumes a "1" state, and the remaining three flip flops each assume a "0" state. This state may be defined as a V-A Delay (VAD) state wherein a prescribed ventricular-to-atrial (V-A) interval is initiated. This V-A interval may be considered as the "atrial escape interval," or "AEI." As soon as the memory control 74 detects that the VAD state has been initiated, as evidenced by the "1000" appearing on the state bus 64, it retrieves from the memory 40 an appropriate data word, previously programmed into the memory 40 from the external programmer 48, that defines the desired length of the AEI; or, when operating in a rate-responsive mode, it retrieves the SIR signal (or a signal derived from the SIR signal) as such AEI-defining data word. The AEI data word is sent to one of the programmable timers 76 and sets the length of the time period that is to be measured during the VAD state.

The timers 76 are essentially just counters that count down (or count up), using a specified clock signal, to the value specified in the data word. When the counting has been completed, and assuming that a given counter has not been reset by the occurrence of a P-wave, the given one of the counters or timers 76 is said to have "timed-out," and an appropriate time-out signal is generated that is sent to the time-out decode logic 78. The decode logic, in turn, recognizes that the current state of the system is the VAD state (as determined by monitoring the state bus 64), and therefore that the AEI has timed-out without any cardiac activity having been sensed. Hence, an A-pulse trigger signal is generated and sent to the A-pulse generator 18, so that the atrium can be stimulated. At the same time, an appropriate logic signal(s) is sent to the state logic 62 over the signal line(s) 80 to alert the state logic to the fact that the timer 76 has timed-out.

The state logic 62, in response to receiving the signal(s) from the time-out decode logic 78, and also in response to the current VAD state, triggers the next state of the prescribed sequence. For DDD operation, this state is typically a blanking state, or BLANK state, during which the P-wave and R-wave sense amplifiers, 22 and 24, are disabled. Accordingly, the state logic generates appropriate signal(s) on signal lines 36 and 38 to blank the P-wave sense amplifier 22 and the R-wave sense amplifier 24, and also causes the state registers 60 to change to a BLANK state, which state could be defined, for example, by the flip flops of the state registers 62 assuming a "0001" (hex "1") condition. This BLANK state, detected on the state bus 64, causes the memory control circuitry to retrieve an appropriate data word from memory that defines the length of the blanking interval, which data word is loaded into one of the programmable timers 76. As soon as the timer 76 times-out, indicating that the prescribed blanking interval has elapsed, a time-out signal is generated that is sent to the time-out decode logic 78. Upon receipt of this time-out signal, and in response to the current state being a BLANK state, the time-out decode logic 78 sends an appropriate logic signal to the state logic 62. The state logic 62 responds by steering the state registers 62 to assume the next state in the prescribed sequence, which may be, for example, an A-V delay state.

At the beginning of the A-V delay state, another value is loaded into an appropriate one of the programmable timers 76 that defines the length of the A-V delay, or "AVD." If the AVD timer times-out without being reset, indicating that no R-wave has been sensed, the decode logic generates a V-pulse trigger signal, and notifies the state logic 62 of this event. The state logic, in turn, causes the next appropriate state to be entered, which state may be another blanking state, or BLANK state, similar to the one described above, but having perhaps a different duration. At the conclusion or timing out of this second BLANK state, the next state in the prescribed sequence is initiated, which state may be a refractory (REF) state.

In the manner described above, the control system 26 assumes one state after another, thereby controlling the operation of the pacemaker. In general, a state is changed when a specified one of the timers 76 times-out, or when a prescribed event occurs.

It is noted that the state of the control system could also be changed by receipt of an appropriate command from the telemetry system.

The control system 26 of FIG. 2 may be realized using dedicated hardware circuits, or by using a combination of hardware and software (or firmware) circuits. The appropriate sequence of states for a given mode of operation, such as DDD or VDI, for example, can be defined by appropriate control of the memory control 74 and the state logic 62. These circuit elements, in turn, are most easily controlled through an appropriate software or firmware program that is placed or programmed into the pacemaker memory circuits. The manner of accomplishing such programming is known in the art.

A detailed description of the various circuits of the control system 26 of FIG. 2 is not presented herein because all such circuits are conventional, or may be patterned after known circuits available in the art. Reference is made, for example, to U.S. Pat. No. 4,712,555 wherein a state machine-type of operation for a pacemaker is described; U.S. Pat. No. 4,788,980, wherein the various timing intervals used within the pacemaker and their inter-relationship are more thoroughly described; and U.S. Pat. No. 4,944,298 wherein an atrial-rate based programmable pacemaker is described, including a thorough description of the operation of the state logic used to control such a pacemaker. The '980 and '298 patents are incorporated herein by reference.

Figure 3:
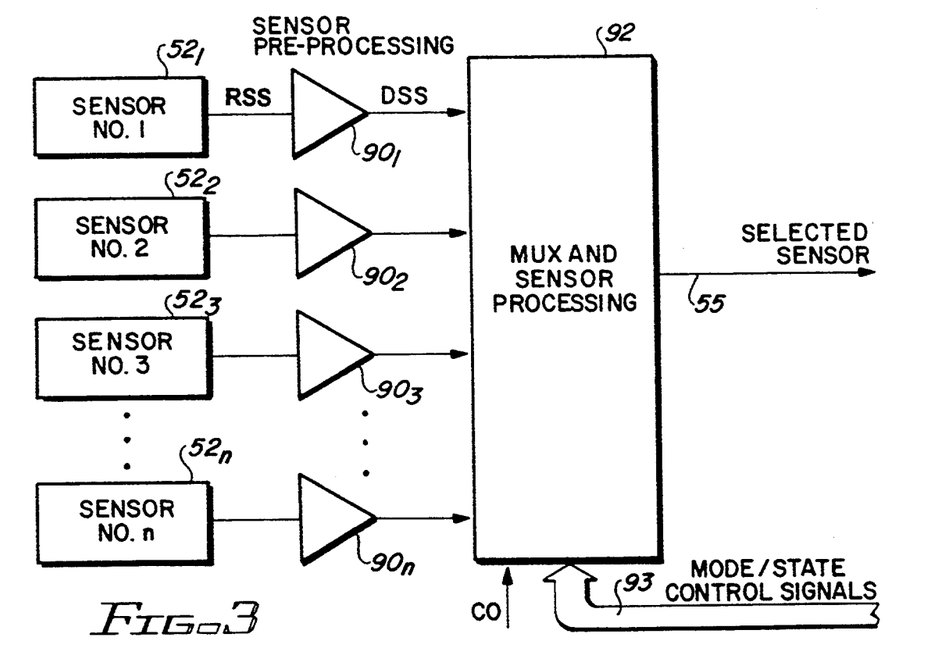
FIG. 3 is a functional block diagram of the sensor selection circuitry of FIG. 2.

Of particular significance to the present invention is the sensor selection circuitry 71. A functional block diagram of the sensor selection circuitry 71 is shown in FIG. 3. As seen in FIG. 3, a plurality of sensors $52_1$, $52_2$, ... $52_n$ each generate a raw sensor signal as a function of a sensed physiologic-related parameter of the patient, e.g., physical activity, blood oxygen saturation, blood pH, respiration rate, and the like. Such raw sensor signals are received and pre-processed in sensor pre-processing circuits $90_1$, $90_2$, ... $90_n$.

Figures 4, 5:
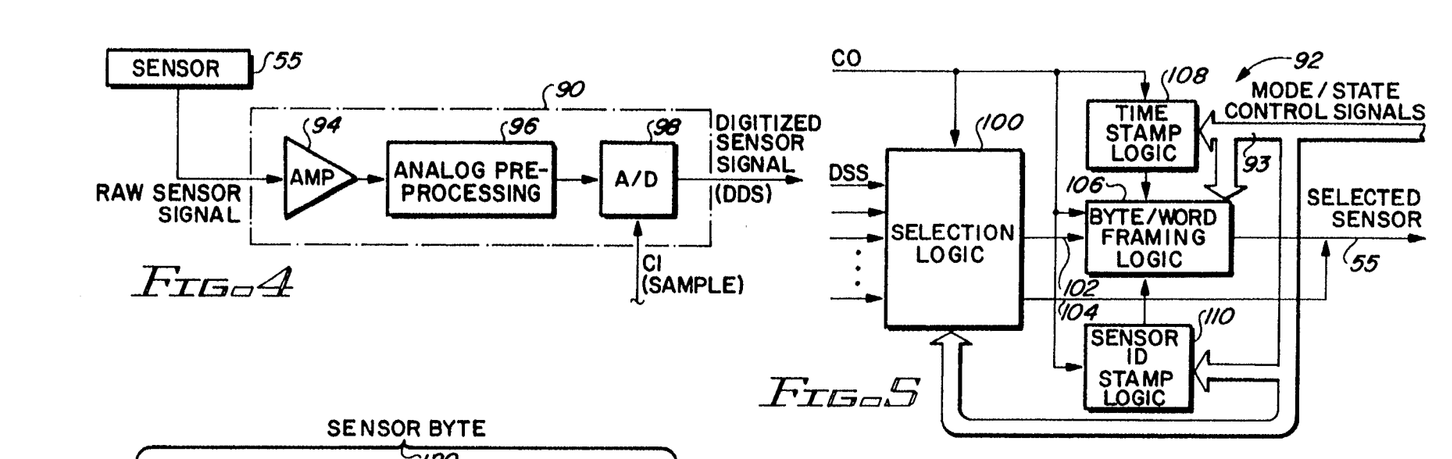
FIG. 4 is a functional block diagram of the sensor pre-processing circuits of FIG. 3.
FIG. 5 is a functional block diagram of the multiplexer (MUX) and sensor processing circuits of FIG. 3.

A representative pre-processing circuit 90 is shown in FIG. 4. Such pre-processing circuit 90 assumes that the raw sensor signal is an analog signal, which is usually the case for most physiological sensors 55. The raw sensor signal is first amplified by amplifier 94, and then subjected to analog pre-processing by circuit 96. The analog pre-processing carried out by circuit 96 normally includes threshold detection and filtering, and may also include limiting, as is known in the art. However, such analog pre-processing may include any desired analog signal pre-processing that enhances the informational content of the raw sensor signal, i.e., that enhances the ability to detect the physiologic-related parameter represented by the raw sensor signal. The pre-processed signal is then converted to a digital sensor signal (DSS) by an analog-to-digital (A/D) converter 98, which A/D converter may be of conventional design. In a preferred embodiment, the A/D converter 98 converts the analog pre-processed signal to a 5-bit normalized digital word, which 5-bit normalized digital word represents a normalized DSS.

Should a particular sensor 55 output a pulse train, i.e., a series of pulses of varying width and spacing, as would be the case, e.g., if a motion sensor of the type shown in U.S. Pat. Nos. 4,771,780 and 4,846,195 were used, then the sensor preprocessing circuit 90 would be different than what is shown in FIG. 4. Pre-processing of a pulse grain signal would typically include a conventional line receiver (or buffer) circuit for receiving the pulse train signal, and a circuit for measuring the frequency of the pulses, e.g., a conventional rate-determining circuit that measures the average time period between pulses during a prescribed base time period. An A/D converter would then be used to convert the measured frequency (which would represent a measure of the motion sensed by the sensor) to a digital word, or DSS.

Returning again momentarily to FIG. 3, it is seen that the DSS from each sensor pre-processing circuit $90_i$, where the subscript i represents a sensor index integer, is presented to a multiplexer (MUX) and sensor processing circuit 92. The MUX and sensor processing circuit 92 selects one of the DSS's and processes it in a prescribed manner, and makes such selected and processed signal available as the selected sensor signal, on signal line 55. (It is noted that a signal appearing on a specific signal line, referenced by a given reference numeral, may hereafter be referred to as the signal of such given reference numeral; e.g., the selected sensor signal appearing on signal line 55 may be referred to as "the selected sensor signal 55.")

In accordance with the present invention, the MUX and sensor processing circuit 92 selectively operates in one of a plurality of operating modes, as determined by the mode/state control signals received from the sensor selection and rate-determining logic 70 over control bus 93. In a first mode, which may be considered as a normal rate-responsive mode, the MUX and sensor processing circuit functions primarily as a multiplexer circuit, i.e., a switch, that momentarily selects a given one of the DSS inputs received from the sensor pre-processing circuits $90_i$ and presents such selected signal as the selected sensor signal 55 to the sensor-selection and rate-determining logic 70. Several DSS's may be selected by the MUX circuit 92 in this fashion within a given cardiac cycle, or within a specified number of cardiac cycles. The SIR signal is then derived or generated from such selected signal or signals by the sensor-selection and rate-determining logic 70 (FIG. 2) in accordance with a specific SIR-defining function.

In a second mode, which may be considered as a sensor event recording mode (or simply a "sensor recording mode"), the MUX and sensor processing circuit 92 functions as both a multiplexer and processing circuit to systematically select a plurality of DSS's, forming each selected DSS into an appropriate sensor word, and compiling a plurality of such sensor words, corresponding to sensor signals obtained at approximately the same time, into a sensor byte. The sensor byte is then presented as the selected sensor signal 55, and is stored in an appropriate address within the memory 40 of the pacemaker.

Referring to FIG. 5, a functional block diagram of the MUX and sensor processing circuit 92 is shown. As seen in FIG. 5, the DSS's are directed to selection logic 100, which selection logic may be a conventional n-to-1 MUX circuit, where n is an integer representing the number of sensors 52 that are used. Included within the selection logic 100 is appropriate logic circuitry for directing the selected DSS output to either signal line 102, when operating in a sensor recording mode, or to signal line 104, when operating in a conventional rate-responsive mode. Note that signal line 104 is connected to the output signal line 55 of the MUX and sensor processing circuit 92, so that when in the conventional rate-responsive mode, the DSS selected by the selection logic 100 becomes the selected sensor signal 55.

When the MUX and sensor processing circuit 92 are operating in a sensor recording mode, then the selection logic 100 places the selected DSS on signal line 102. Such selected DSS is then directed to byte/word framing logic 106, where an appropriate sensor word, and sensor byte are formed, and presented as the selected sensor signal 55. Time stamp logic circuitry 108, and sensor ID (identification) stamp logic 110 interface with the byte/word framing logic 106 so that appropriate time information, and sensor ID information, can be incorporated into the sensor byte that is thus formed. The time stamp logic 108 determines the appropriate time based on the mode/state control signals, received over control bus 93, and an appropriate clock signal C0, obtained from the oscillator 82 and/or clock logic 84 (FIG. 2). Such time is preferably measured relative to the beginning of a particular event, such as the beginning of an exercise protocol, as explained below.

Figure 6:
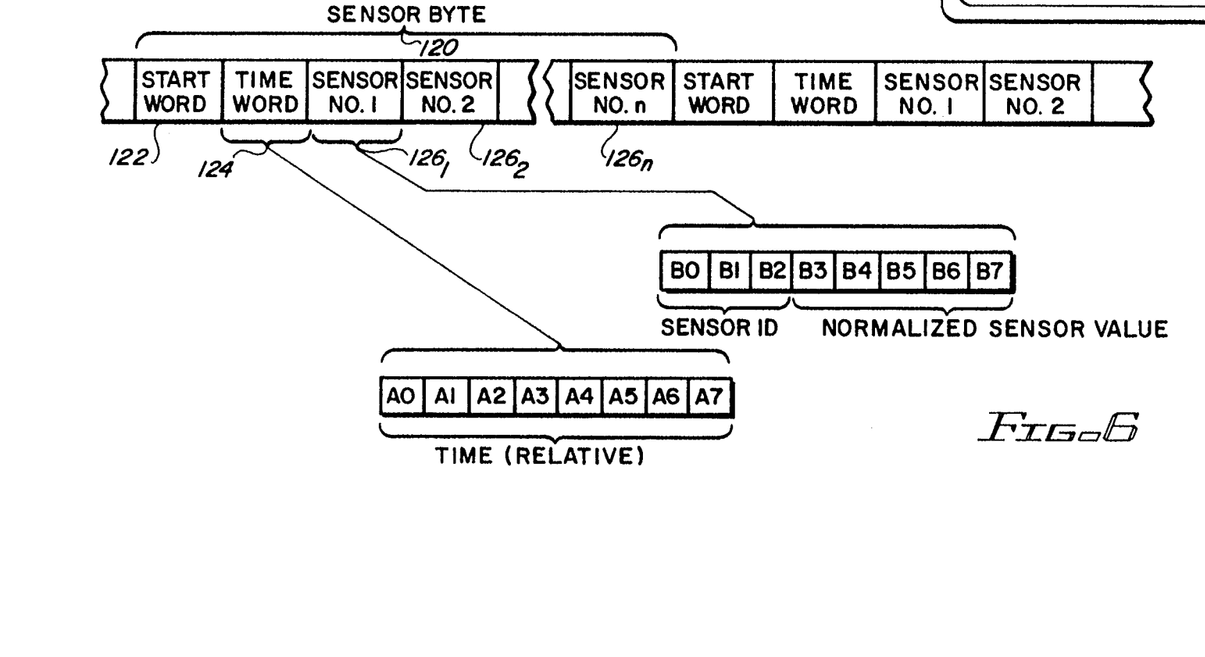
FIG. 6 diagrammatically illustrates a sequence of sensor bytes formed for storage in the memory of the pacemaker in accordance with the present invention.

One manner in which the sensor byte may be formed is diagrammatically illustrated in FIG. 6. As seen in FIG. 6, a sensor byte 120 comprises a start word 122, a time word 124 and a plurality of sensor words $126_1$, $126_2$, ... $126_n$. Each word includes a fixed number of bits, e.g., eight bits. The start word includes a specified pattern of bits that uniquely identifies it as the start of a sensor byte 120. An exemplary start word bit pattern is "11111111." The time word 124 contains a digital word that represents the relative time at which the sensor words $126_i$ in the sensor byte 120 were obtained. The resolution of such time word may be any convenient time, such as one second. Thus, for example, if the eight bits of a given time word 124 are "00010011" (which is the binary equivalent of nineteen), and if the resolution time is one second, that means that the sensor words $126_i$ included with such time word occurred (were obtained or measured) at a relative time of 19 seconds from when the recording of sensor events began.

The sensor words 126 include two portions. A first portion, e.g., the first three bits, B0, B1 and B2, may comprise a sensor ID portion, thus allowing up to eight different sensors to be identified. The last portion, e.g., the last five bits, B3, B4, B5, B6 and B7, may comprise the normalized DSS, thus allowing the DSS to assume any one of thirty-two values, ranging between 0 (a minimum DSS) to 31 (a maximum DSS).

Once the sensor byte 120 is compiled by the MUX and sensor processing circuitry 92, it is made available to the memory control circuit 74 (FIG. 2) over the selected sensor signal line 55, and stored in the pacemaker memory 40 at an appropriate address. Advantageously, the time required to compile and form a given sensor byte is only a small fraction of a cardiac cycle. Thus, once a given sensor byte is compiled and stored, the MUX/sensor processing circuitry 92 reverts to its normal rate-responsive operating mode, until such time as the next sensor byte is to be compiled, e.g., in the next cardiac cycle, or after five cardiac cycles, or after whatever the sensor sample time period may be. In this manner, the normal rate-responsive operating mode of the pacemaker need not be interrupted while the sensor bytes are formed and stored. Rather, the sensor recording mode, i.e., the mode during which the sensor bytes are formed and stored, may simply be interleaved inbetween the normal operation of the pacemaker.

As an alternative to time stamping the selected DSS within the sensor byte, as described above, it is noted that the appropriate time information may be stored by time logging the selected DSS and sensor ID information into sequential addresses within the pacemaker memory 40. In accordance with such "time logging," specific addresses within the pacemaker memory are allocated to DSS and sensor ID information obtained at a particular time. Thus, when the DSS and sensor ID information is retrieved from the memory, the relative time at which such information occurred is also obtained based on the memory address from which the information was retrieved.

Figure 71:
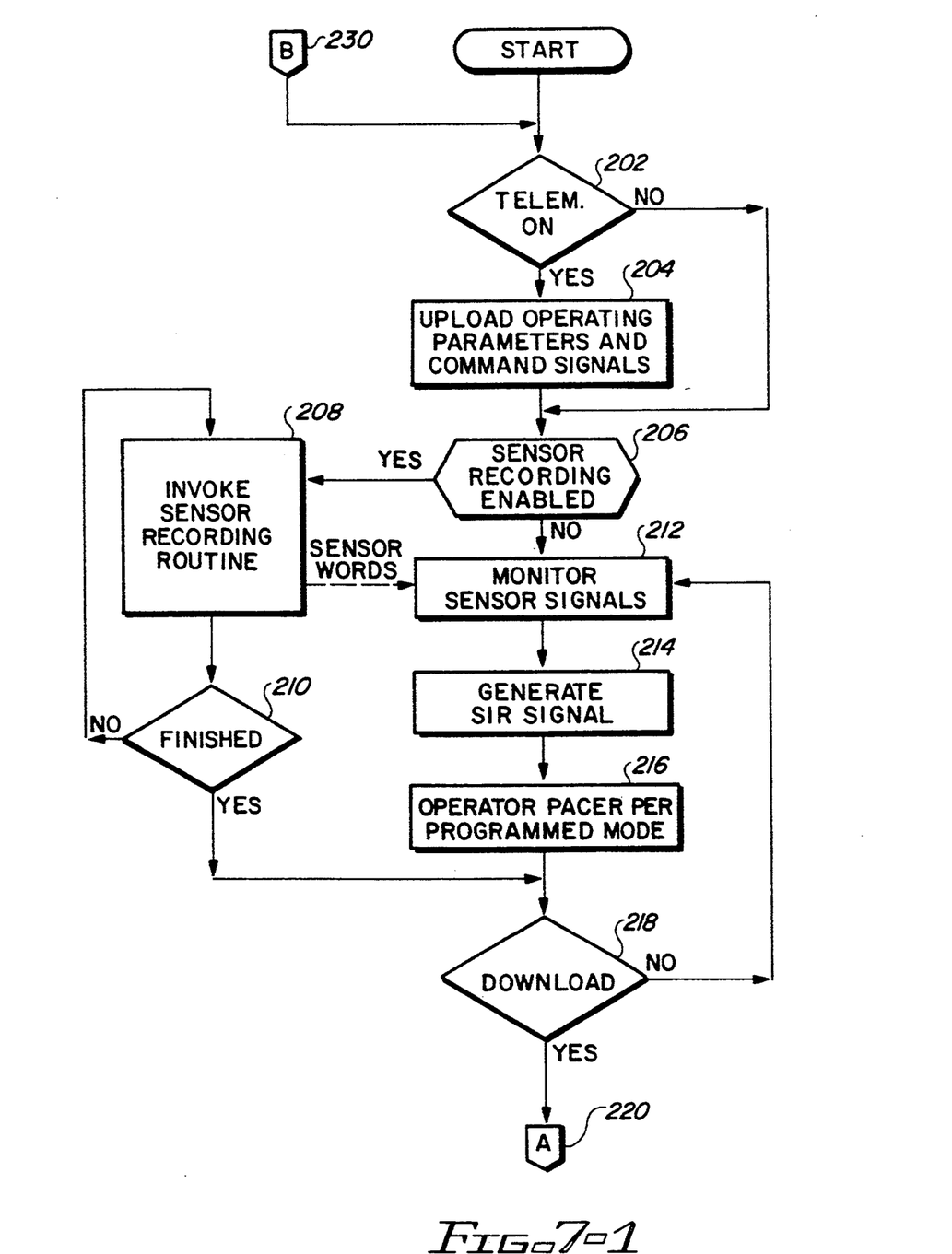
Figure 72:
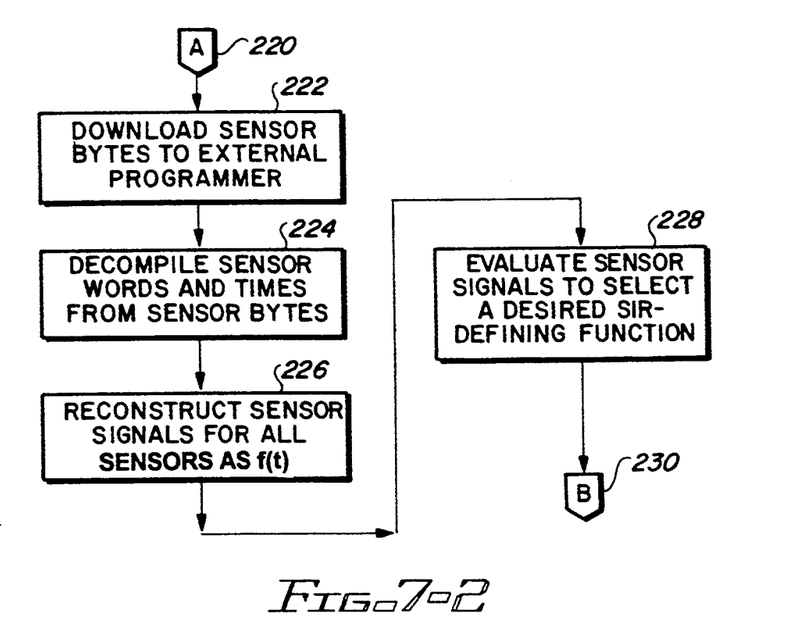

Turning next to FIGS. 7-1 and 7-2, a flowchart is shown that illustrates the operation of a pacemaker having a sensor event recording feature in accordance with the present invention. It is noted that in FIG. 7-1 and 7-2, and in the other flowcharts presented herein, each main step of the method being illustrated is depicted as a "box" or "block," with each box or block having a reference numeral assigned thereto. Further, each box or block is connected to other boxes or blocks with a directional line that indicates the flow from one step to the next.

The method shown in FIGS. 7-1 and 7-2 advantageously allows an optimum SIR-defining function to be determined for use within a rate-responsive pacemaker implanted within a particular patient. Basically, such method involves: (a) having the patient perform a specified exercise protocol; (b) sampling each of the plurality of sensors used with the pacemaker to obtain a respective sampled physiological signal while the patient is performing the specified exercise protocol; (c) storing each of the respective sampled physiological signals in the memory circuit of the pacemaker as the sampled physiological signals are obtained; (d) terminating the exercise protocol; (e) downloading the stored physiological signals from the pacemaker memory circuit to an external programmer; (f) evaluating the downloaded physiological signals and defining the SIR signal to be a specified function thereof; and (g) uploading the specified function to the memory circuit of the pacemaker.

Starting with FIG. 7-1, it is seen that a first step of the method involves making a determination as to whether the telemetry circuits of the pacemaker are enabled or turned ON (block 202). The telemetry circuits of an implantable pacemaker, as is known in the art, are typically turned ON by placing a telemetry head (which is part of an external programmer device 48) on the patient near the location where the pacemaker is implanted. A magnet in the telemetry head then causes a magnetic reed switch within the pacemaker to close, which action turns ON the telemetry circuits. If the telemetry circuits are ON, then appropriate command signals and/or operating parameters may be uploaded (block 204) from an external programmer, or equivalent device, to the memory circuits of the pacemaker, in conventional manner. In accordance with the present invention, one of the operating commands thus uploaded is a command that enables or disables the sensor recording mode.

If the sensor recording mode is enabled (block 206), then an appropriate sensor recording routine is invoked (block 208), as explained more fully below in conjunction with FIG. 8. As part of the sensor recording process (block 208), various digitized sensor signals (DSS's), or sensor words containing a DSS, are sampled and monitored (block 212). From these monitored DSS's, an SIR signal is generated (block 214), and the pacemaker continues to operate in accordance with a programmed mode (block 216), e.g., by supplying stimulation pulses on demand at a rate determined by the SIR signal, in conventional manner.

At any time during the normal operation of the pacemaker (block 216), or when sensor recording is completed (block 210), a determination is made as to whether any data stored in the pacemaker memory, e.g., the sensor data recorded during the sensor recording routine, is to be downloaded to the external programmer (block 218). If not, then the normal rate-responsive operation of the pacemaker continues (blocks 212, 214, 216, 218). Note also that the normal rate-responsive operation of the pacemaker continues in the event that the telemetry circuit is not turned ON (as determined at block 202), and sensor recording is disabled (as determined at block 206). If downloading is to be done (as determined at block 218), then the sensor bytes (and any other selected data) stored in the pacemaker memory are downloaded to an external programmer (block 222). Note that block 222 is shown in the flowchart of FIG. 7-2, which flowchart is a continuation of FIG. 7-1 through the connector block "A" (block 220).

Once the sensor words are received at the external programmer (block 222 of FIG. 7-2), such words are decompiled (block 224) in order to extract the sensor signal information therefrom. Advantageously, such sensor signal information includes not only the digital sensor signal (DSS) for a particular sensor, but also the relative time at which the DSS was obtained. Thus, the sensor signals for each sensor as a function of time are reconstructed (block 226). From such reconstruction, and knowing the type of exercise protocol that the patient experienced at the time the sensor signals were recorded, the sensor signals are evaluated in order to determine what weighted combination thereof could be used to generate an SIR signal that provides the most hemodynamically beneficial pacing rate for the patient (block 228). Such SIR signal, or more accurately a specified function that defines such an SIR signal as a function of the various sensor parameters, may then be uploaded to the pacemaker (block 204, FIG. 7-1) for use by the pacemaker thereafter as it carries out its normal rate-responsive operation (blocks 212, 214, 216). Thus, in this manner, the sensor signals are recorded while the patient is undergoing a known exercise protocol, and such sensor signals are later evaluated in order to determine an appropriate SIR-defining function for that particular patient.

Figure 8:
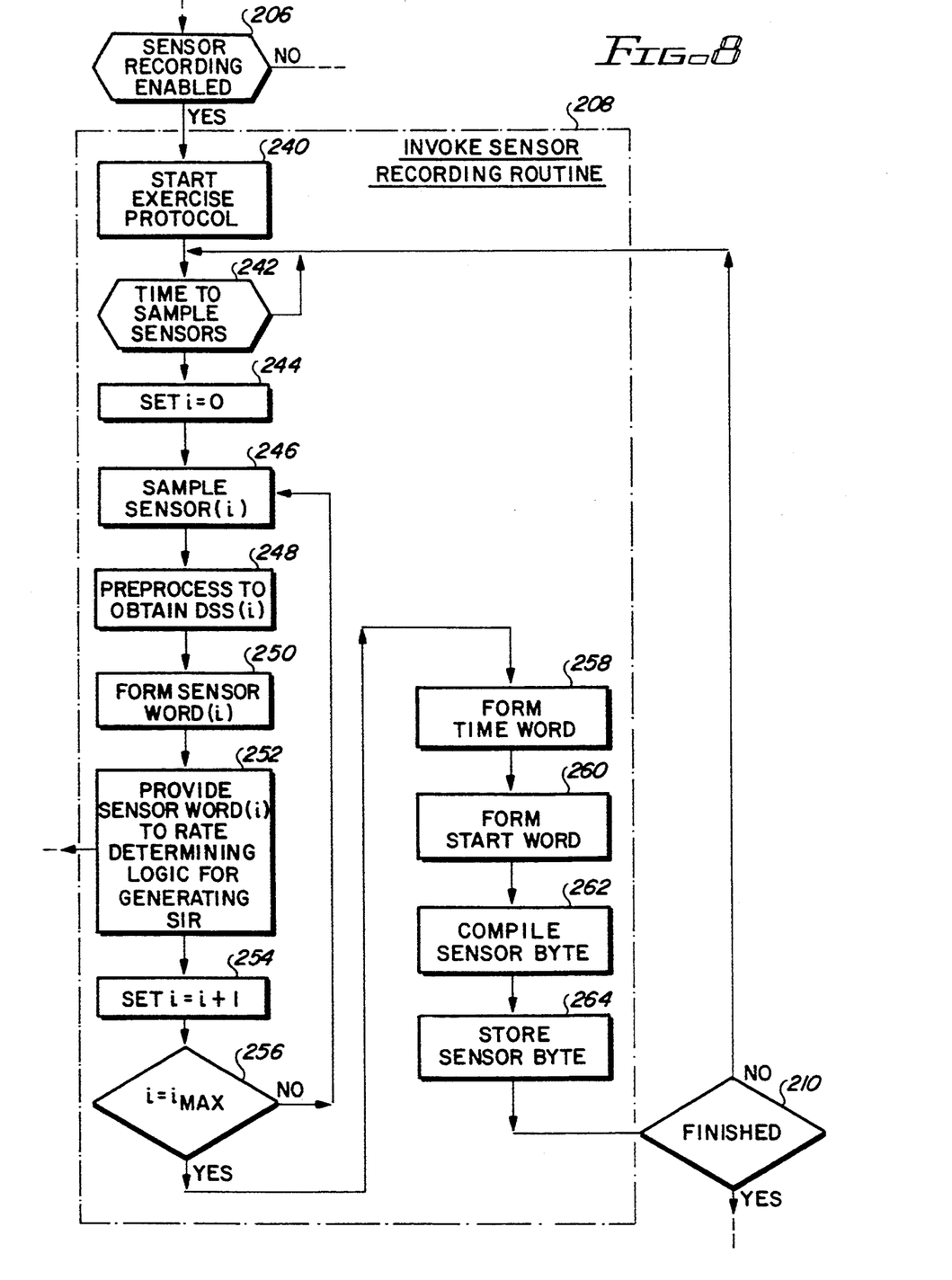
FIG. 8 is a flowchart that illustrates one technique for recording sensor events in accordance with the operation shown in FIGS. 7-1 and 7-2.

Turning next to FIG. 8, there is shown a flowchart that illustrates one sensor recording routine or technique that may be invoked at block 208 of the method shown in FIG. 7-1. As seen in FIG. 8, after a determination is made that sensor recording is enabled (block 206), a specified exercise protocol is begun (block 240). Such exercise protocol may involve walking or jogging on a treadmill, walking up and down a flight of stairs, or the like. While such exercise protocol is being carried out by the patient, a determination is made as to whether it is time to sample the various sensors that are used with the pacemaker (block 242). The sensors may be sampled at specified intervals, e.g., every cardiac cycle, every five cardiac cycles, every ten cardiac cycles, every 30 seconds, etc. The sampling time is preferably a programmable option that is selected by the physician at the time the pacemaker is implanted.

If it is time to sample the sensors (block 242), then a sensor index variable i is set equal to zero (block 244), and a corresponding sensor, sensor(i), is sampled (block 246). The sampled sensor signal is then pre-processed to obtain a corresponding DSS(i) (block 248). An appropriate sensor word, Sensor-Word(i), is then formed containing the sensor ID, determined from the sensor index variable i, and the DSS(i) (block 250). Such Sensor-Word(i) comprises the selected sensor signal 55 that is made available to the rate determining logic 70 (FIG. 2) during normal operation of the rate-responsive pacemaker, and from which an appropriate SIR signal is generated (block 252). The value of the sensor index is incremented (block 254), and the process repeats (blocks 246, 248, 250, 252, 254) until all the sensors have been sampled, i.e., until the sensor index i is equal to a maximum value (block 256).

When all the sensors have been sampled, a time word is formed (block 258). The time word includes an indication of the relative time, i.e., relative to when the exercise protocol began, at which the sensors were sampled. Advantageously, the time required to sample a given sensor is very short, e.g., 1–5 milliseconds or less, so all of the sensors can be sampled within a relatively short time. Thus, for purposes of forming the time word (at block 258), it can be assumed that all of the sensors were effectively sampled at the same time.

After the time word has been formed, the start word is formed (block 260). As previously indicated, the start word comprises a fixed unique sequence of bits that identifies the start of a given sensor byte. With the start word formed, the sensor byte can thus be formed (block 262). As indicated in FIG. 6, the sensor byte includes the start word, the time word, and a sensor word for each sensor that was sampled at the time indicated in the time word. Once formed, the sensor byte is stored in the pacemaker memory (block 264). If additional samples of the sensors are to be made (block 210), and if it is time for the next sample to be made (block 242), then the sampling process repeats (blocks 246–264). Typically, samples of the physiological sensors will be made throughout a significant portion of the exercise protocol, although for some patients, sufficient samples may be obtained during the first few minutes of the exercise protocol. Ideally, sensor samples will be obtained during periods of time when the heart rate is normal (no exercise), when the heart rate is increasing (at the onset of exercise), and when the heart rate is decreasing (immediately after exercise has been concluded).

Figure 9:
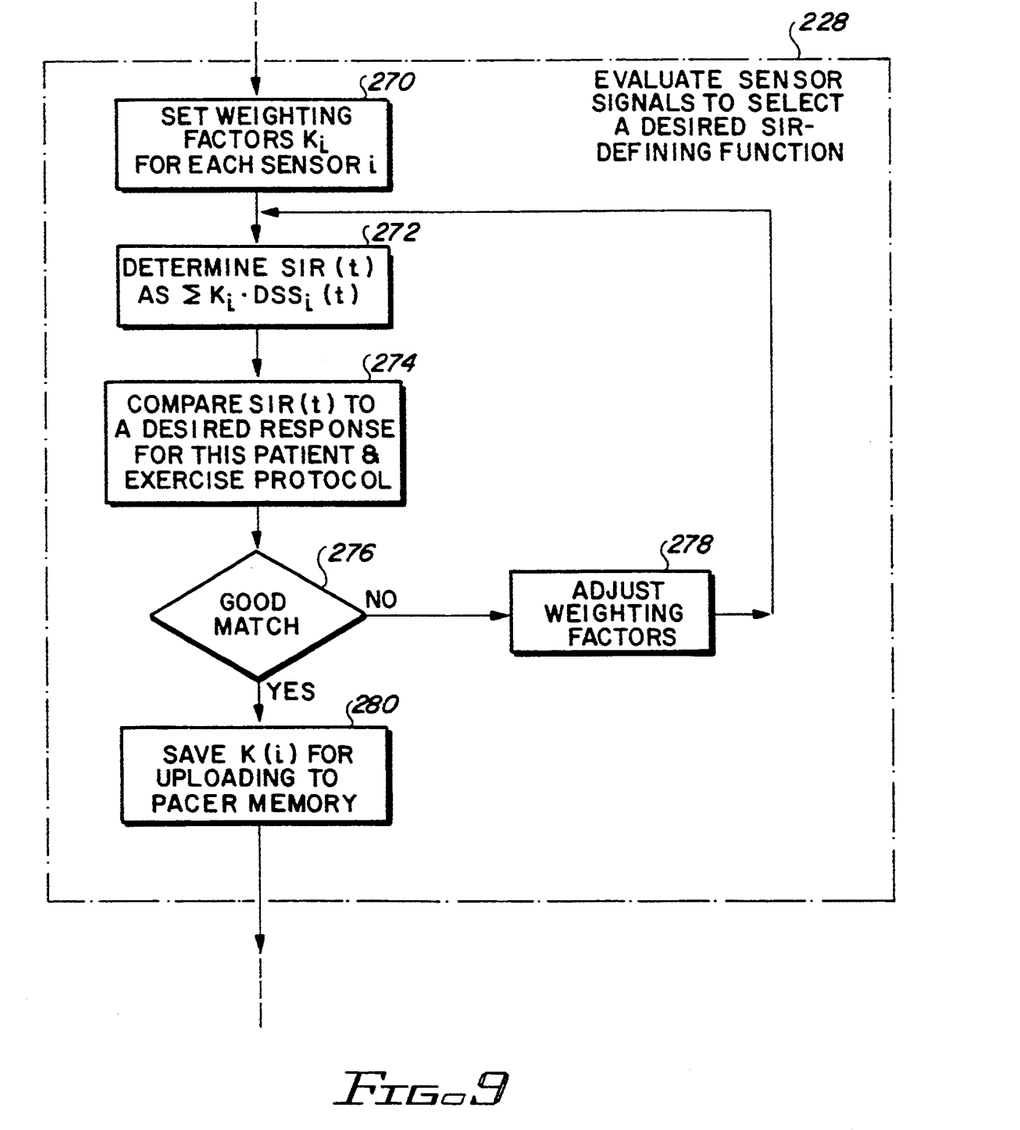
FIG. 9 is a flowchart depicting how the recorded sensor events may be subsequently analyzed to determine an optimum function that defines the sensor indicated rate (SIR) signal.

Turning next to FIG. 9, a flowchart is shown depicting a method that may be used to evaluate the recorded sensor signals in order to determine an appropriate function that may thereafter be used to define the sensor indicated rate (SIR) signal. The evaluation shown in FIG. 9 thus represents one type of evaluation that may be performed in block 228 of FIG. 7-2.

As seen in FIG. 9, a first step of the evaluation process involves setting weighting factors $k_i$ for each of the i sensors (block 270). Initially, such weighting factors may be somewhat arbitrary, e.g., making all the weighting factors equal (so that if there are five sensors, each $k_i$ is set equal to 0.2). Next, an SIR signal is derived for each sample time based on the sum of the DSS signals for a particular sample time multiplied by their respective weighting factors. The combination of all such SIR signals for all sample times thus provides an indication of the SIR signal as a function of time, SIR(t) (block 272). That is $$SIR(t) = \Sigma k_i \cdot DSS_i(t)$$

for all i and t, where i represents the number of sensors, t represents the sample times, and $DSS_i(t)$ represents the digitized sample signal at a particular sample time, t. The SIR(t) signal thus obtained is compared to a desired sensor indicated rate for the patient given the particular exercise protocol to which the patient was subjected when the sensor samples were made (block 274). If there is not a good match between SIR(t) and the desired sensor indicated rate, as determined at block 276, then the weighting factors are adjusted in an appropriate manner (block 278), and the process is repeated (blocks 272, 274, 276). If there is a good match (block 276), then the weighting factors, and any other SIR-defining parameters, are saved for uploading to the pacemaker memory (block 280).

Advantageously, because the evaluation process of FIG. 9 may be carried out "off line," i.e, after the exercise protocol has been completed, numerous variations of the weighting factors can be readily tested to quickly determine an optimum SIR(t) signal. Moreover, it should be emphasized that the weighting factors $k_i$ need not necessarily be constants. They too may be a function of the sample time, so that a given sensor signal is weighted more heavily during the onset of exercise than it is when the exercise activity is stabilized, or when the exercise activity is decreasing. In this manner, then, a truly effective SIR-defining function may be determined, with minimal patient/physician interface, thereby providing an SIR signal that matches a hemodynamically beneficial pacing rate for a particular patient.

As described above, it is thus seen that the present invention provides a multi-sensor rate-responsive pacemaker wherein each of the plurality of sensor signals is selectively stored in a memory circuit of the pacemaker. Such signals are thereafter downloaded to an external programmer, or equivalent external processing/computing device, for non-real time processing, thereby enabling a non-real time analysis of different combinations of the sensor signals, including different weighting factors, in order to arrive at a hemodynamically beneficial SIR rate.

As further seen from the above description, the invention provides an efficient way to safely and easily assess which of plural sensor outputs, or combinations of plural sensor outputs, used by a multi-sensor rate-responsive pacemaker provides the most hemodynamically beneficial results for a given patient at a given time.

Still further, it is seen that the invention provides a more effective, less expensive way to perform the patient tests and trials that are needed to assess whether a given selection or weighting of plural sensor output signals is best suited for a given patient.

While the invention herein disclosed has been described by means of specific embodiments and applications thereof, numerous modifications and variations could be made thereto by those skilled in the art without departing from the scope of the invention set forth in the claims.

What is claimed is:

1. A method of determining an optimum sensor indicated rate (SIR) signal for use with a multi-sensor rate-responsive pacemaker implanted in a patient, said pacemaker having: a plurality of sensors, each being adapted to sense a physiologic-related parameter and to generate a physiological signal indicative of such sensed physiologic-related parameter; a sense amplifier that senses natural cardiac contractions; a pulse generator that selectively generates stimulation pulses on demand at a rate determined by the SIR signal; and a memory circuit, said method comprising the steps of:

(a) having the patient perform a specified exercise protocol;

(b) sampling each of the plurality of sensors to obtain a respective sampled physiological signal while the patient is performing the specified exercise protocol;

(c) generating a plurality of sensor byte signals, each sensor byte signal comprising respective sampled physiological signals appropriately time stamped to indicate when the sampled physiological signals were obtained relative to specified exercise protocol performed in step (b), and storing the sensor byte signals in the memory circuit;

(d) terminating the specified exercise protocol;

(e) downloading the stored sensor byte signals from the pacemaker memory circuit to an external programmer;

(f) extracting the physiological signals and time stamped information from the downloaded sensor byte signals, evaluating the extracted physiological signals in light of the time stamped information that indicates when the extracted physiological signals were obtained relative to the specified exercise protocol, and defining said SIR signal to be a specified function of said physiological signals; and (g) uploading said specified function to the memory circuit of said pacemaker;

whereby said specified function thereafter defines said SIR signal.

2. An implantable rate-responsive pacemaker system, comprising:

a plurality of sensors, each being adapted to sense a physiologic-related parameter of a patient and to generate an individual sensor signal indicative of such sensed physiologic-related parameter, whereby a plurality of sensor signals are generated;

means for generating a set of weighting control signals;

implantable processing means responsive to the plurality of sensor signals and the set of weighting control signals for generating a sensor indicated rate (SIR) signal, the SIR signal being a prescribed weighted combination of a selected plurality of said plurality of sensor signals as defined by said set of weighting control signals;

implantable pulse generator means for generating stimulation pulses at a rate that varies as a function of the SIR signal;

memory means coupled to said implantable processing means for storing the plurality of sensor signals;

telemetry means coupled to the memory means and the implantable processing means for establishing a data link between the memory means and a receiving location external to the implantable pulse generator means;

the implantable processing means further including means for generating a plurality of sensor byte signals, each sensor byte signal including the plurality of sensor signals stored in the memory means and a time stamp that identifies when each of the plurality of sensor signals was generated, the plurality of sensor byte signals being downloadable through the data link; and an external processor coupled to the telemetry means to receive the plurality of sensor byte signals, the external processor including means for recovering the plurality of sensor signals contained within the plurality of sensor byte signals, means for analyzing various combinations of the individual sensor signals contained within the plurality of sensor signals, wherein the means for generating the set of weighting control signals generates such control signals as a function of such analysis, and means for uploading the set of weighting control signals through the data link for use by the implantable processing means.

3. The rate-responsive pacemaker system, as set forth in claim 2, further including:

sampling means for sampling each of the plurality of sensors at least once during each n cardiac cycles to generate a plurality of sampled sensor signals, where n is a prescribed integer; and means for combining the plurality of sampled sensor signals to produce one of the plurality of sensor byte signals, with a new sensor byte signal being generated each n cardiac cycles.

4. The rate-responsive pacemaker system, as set forth in claim 3, further including:

means for normalizing each of the plurality of sampled sensor signals included within the sensor byte signal so that each assumes a value between prescribed minimum and maximum values.

5. The rate-responsive pacemaker system, as set forth in claim 2, wherein the implantable processing means operates in a selected one of a plurality of operating modes, said plurality of operating modes including:

a rate-responsive mode, during which the implantable pulse generator means generates stimulation pulses at a rate determined by the SIR signal; and a sensor event recording mode, during which the sensor byte signals are formed and stored.

6. The rate-responsive pacemaker system, as set forth in claim 5, herein the implantable processing means includes means for interleaving its operation between the rate-responsive mode and the sensor event recording mode, with the sensor event recording mode being invoked to form a sensor byte signal once every n cardiac cycles, and with the rate-responsive mode being carried out at all other times.

7. An implantable pacemaker, comprising:

a plurality of sensors, each being adapted to sense a respective parameter and to generate a sensor signal indicative of such sensed parameter;

sensor processing means coupled to said plurality of sensors for forming a sensor byte signal, the sensor byte signal having:

a time word that defines a particular sensor sampling time, and a plurality of sensor words, each of said plurality of sensor words including a sensor identification code that identifies a particular one of the plurality of sensors, and the sensor signal generated by the particular one of the plurality of sensors at the particular sampling time defined by the time word;

pulse generator means for generating stimulation pulses responsive to a sensor indicated rate (SIR) signal, the SIR signal being a function of a prescribed combination of said sensor signals; and means for downloading the sensor byte signal to an external processor remote from the implantable pacemaker.

8. The implantable pacemaker of claim 7, further including:

memory means for selectively storing said sensor signals from each of said plurality of sensors at the prescribed sampling time, and wherein the sensor processing means utilizes the sensor signals stored in the memory means in order to form the sensor byte signal.

9. The implantable pacemaker of claim 8, wherein the sensor byte signal further includes a start word that separates the sensor signal words corresponding to a first sampling time from the sensor signal words corresponding to another sampling time.

10. The implantable pacemaker of claim 8, wherein the pulse generator means includes:

means for operating said pacemaker in a pacing mode, characterized by generating stimulation pulses on demand at a rate determined by the SIR signal when of a natural cardiac contraction fails to occur; and a recording mode, characterized by storing the sensor signals in the memory means.

11. The implantable pacemaker of claim 10 wherein the recording mode is interleaved with the pacing mode so that the pacemaker normally operates in the pacing mode, but every n cardiac cycles, where n is an integer, the recording mode is initiated to sample the plurality of sensors and store the respective sampled sensor signals in the memory means, whereupon the pacing mode is reinitiated.

12. The implantable pacemaker of claim 11, wherein n is an integer no greater than 15.

13. The implantable rate-responsive pacemaker as set forth in claim 12, wherein said plurality of sensors include:

an oxygen saturation sensor for sensing an oxygen saturation level of blood; and an activity sensor for sensing physical activity.

14. A rate-responsive pacing system including an external programmer device, the system comprising:

a plurality of sensors, each being adapted to sense a respective physiologic-related parameter and to generate a physiological signal indicative of such sensed physiologic-related parameter;

pulse generator means for selectively generating a stimulation pulse and delivering such stimulation pulse to cardiac tissue;

memory means for storing the physiological signal from each of the plurality of sensors;

sensor processing means coupled to the plurality of sensors, pulse generator means, and memory means for generating a sensor indicated rate (SIR) signal and a plurality of sensor byte signals, the SIR signal being used by the pulse generator means to define the rate at which the stimulation pulses are generated, the SIR signal being derived from a specified function of the physiological signals obtained from the plurality of sensors, each of the plurality of sensor byte signals comprising a plurality of sensor words, each sensor word being representative of the physiological signal from one of the plurality of sensors at a prescribed sampling time;

telemetry means for establishing a communication link between the sensor processing means and the external programmer device, the external programmer device comprising:

means for downloading the plurality of sensor byte signals from the sensor processing means, means for processing the physiological signals contained within the sensor words of the plurality of sensor byte signals in order to arrive at a combined physiological signal, and means for uploading the combined physiological signal to the sensor processing means, the combined physiological signal being used to generate the SIR signal.

15. The rate-responsive pacing system, as set forth in claim 14, wherein said plurality of sensors include:
   an oxygen saturation sensor for sensing an oxygen saturation level of blood; and
   an activity sensor for sensing physical activity.

16. The rate-responsive pacing system, as set forth in claim 14, wherein the sensor processing means generates a sensor byte signal every n cardiac cycles, where n is an integer no greater than 20.

* * * * *